(12) United States Patent
Jones et al.

(10) Patent No.: US 8,742,156 B2
(45) Date of Patent: Jun. 3, 2014

(54) ANTI-VIRAL CARBAMIMIDOTHIOIC ACID ESTERS

(75) Inventors: Steven J. Jones, Vancouver (CA); Allan Sik-Yin Lau, Hong Kong (CN); Jianghong An, Vancouver (CA); Hing-Yee Law, Hong Kong (CN); Chun-Wai Davy Lee, Hong Kong (CN)

(73) Assignees: British Columbia Cancer Agency Branch, Vancouver, British Columbia (CA); Versitech Limited, Hong Kong (CN)

( * ) Notice: Subject to any disclaimer, the term of this patent is extended or adjusted under 35 U.S.C. 154(b) by 0 days.

(21) Appl. No.: 13/816,899

(22) PCT Filed: Aug. 12, 2011

(86) PCT No.: PCT/CA2011/050497
§ 371 (c)(1),
(2), (4) Date: Feb. 13, 2013

(87) PCT Pub. No.: WO2012/021991
PCT Pub. Date: Feb. 23, 2012

(65) Prior Publication Data
US 2013/0143961 A1    Jun. 6, 2013

Related U.S. Application Data

(60) Provisional application No. 61/373,807, filed on Aug. 14, 2010.

(51) Int. Cl.
*C07C 275/28* (2006.01)
*C07C 275/70* (2006.01)

(52) U.S. Cl.
USPC .......................................................... 558/6

(58) Field of Classification Search
USPC ............................................................ 558/6
See application file for complete search history.

(56) References Cited

U.S. PATENT DOCUMENTS

| 1,178,242 | A | 4/1916 | Koss |
| 4,178,242 | A | 12/1979 | Fusco |
| 4,264,600 | A | 4/1981 | Abdulla |
| 4,835,168 | A | 5/1989 | Paget, Jr. et al. |
| 5,955,053 | A | 9/1999 | Marzilli et al. |
| 5,986,074 | A | 11/1999 | Marzilli et al. |
| 7,358,313 | B2 | 4/2008 | Blanchard et al. |

FOREIGN PATENT DOCUMENTS

WO    2007/073168    6/2007

OTHER PUBLICATIONS

Glasser (see Journal of Pharmaceutical Sciences, vol. 54, Issue 7, pub. Sep. 16, 2006, p. 1055-1056.*
Grogan et al., "Diisothiuronium Dihydrohalides Salts", J. Org. Chem., Jun. 19, 1953, vol. 18, No. 6, pp. 728-735.
Dains et al., "The Substituted Thio-Ureas V. The Synthesis of Thio-Ureas from Amino-Ehanols and of Thiazolidine Derivatives", J. Am. Chem. Soc., Jul. 3, 1925, vol. 47, pp. 1981-1989.
Atwell et al., "Potential Antitumor Agents. 15. Bisquaternary Salts", J. Med. Chem., Sep. 1974, vol. 17, No. 9, pp. 930-934.
International Patent Application No. PCT/CA2011/050497, International Search Report dated Oct. 25, 2011.

* cited by examiner

*Primary Examiner* — Rebecca Anderson
*Assistant Examiner* — Karen Cheng
(74) *Attorney, Agent, or Firm* — Gail C. Silver; Borden Ladner Gervais LLP

(57) ABSTRACT

Carbamimidothioic acid esters of formula (I) and 2-nitro-N-[4-(pyridin-4-ylamino)phenyl]-4-(quinolin-4-ylamino)benzamide are used for the treatment of influenza, and for the inhibition of a viral RNA-dependent RNA polymerase. Formulae (I), (II).

14 Claims, 2 Drawing Sheets

Figure 1
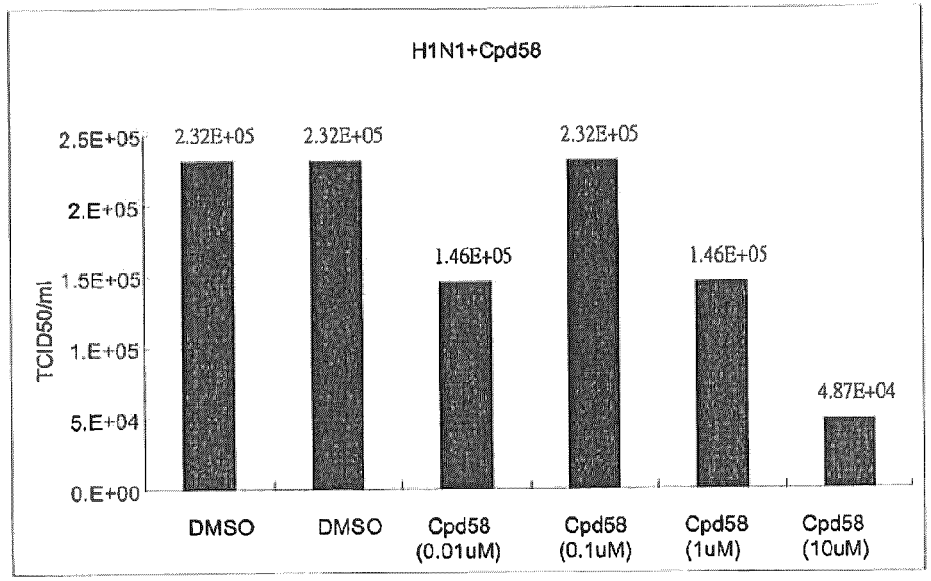
Figure 1A
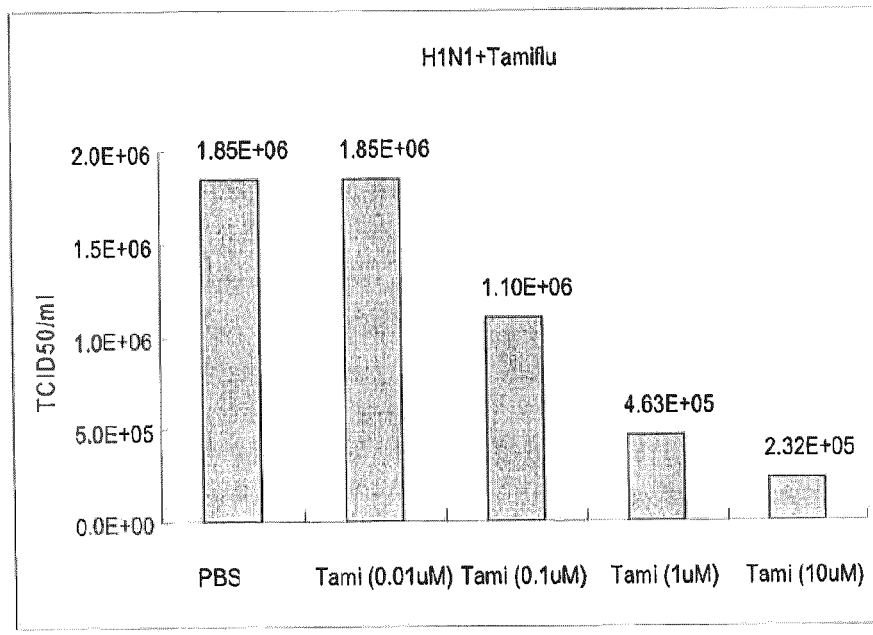
Figure 1B

ANTI-VIRAL CARBAMIMIDOTHIOIC ACID ESTERS

CROSS-REFERENCE TO RELATED APPLICATIONS

This application is a U.S. National Phase Entry of Patent Application No. PCT CA2011/050497, filed Aug. 12, 2011, which claims the benefit of priority of U.S. Provisional Patent Application Ser. No. 61/373,807, filed Aug. 14, 2010.

FIELD OF THE INVENTION

This invention relates to anti-viral compounds, especially those for the treatment of influenza.

BACKGROUND OF THE INVENTION

The impact of influenza infection is felt globally each year when the disease develops in approximately 20% of the world's population. Influenza A virus, in particular, represents a significant health risk to the public. This is due both to its ability to spread quickly within human populations and the high degree of mortality associated with infection. In the last century, three influenza A pandemics in 1918, 1957 and 1968 killed cumulatively over 50 million people. The highly pathogenic H5N1 and H1N1 strains of influenza A virus are emerging as the most likely cause of the world's next major influenza pandemic.

Influenza viruses belong to the family Orthomyxoviridae, and are divided into three (3) genera: Influenza A, Influenza B, and Influenza C. Influenza A can cause epidemics and pandemics in humans and may be transmitted through an animal intermediate host. Influenza B can cause epidemics and has no intermediate host. Influenza C does not occur in epidemics and causes mild disease.

Influenza A viruses are further classified based on the identity of two surface glycoproteins: hemagglutinin and neuraminidase contained in the viral envelope. Nine subtypes of influenza neuraminidases are known, N1 to N9, and sixteen subtypes of hemagglutinin are known, H1 to H16. Thus for instance, influenza A H5N1 refers to an influenza virus which contains the H5 subtype hemagglutinin and the N1 subtype neuraminidase.

Within the viral envelope, the central core contains the viral RNA genome, made up of seven or eight pieces of segmented negative-sense RNA. Each of these RNA segments is separately encapsidated by a nucleoprotein (NP) and associated with one copy of a viral RNA-dependent RNA polymerase. The viral polymerase complex is a heterotrimer composed of two basic proteins, PB1 and PB2, and a more acidic protein, PA. The polymerase and endonuclease activities are carried out by PB1. The PB2 subunit binds to the 5' methylated cap of host-cell pre-mRNAs before they are cleaved to provide primers for viral mRNA synthesis.

Existing influenza medicines include oseltamivir (Tamiflu®) and zanamivir (Relenza). These function by inhibiting neuraminidase, resulting in the inhibition of the release of newly formed virions from the infected cells. However, there have been several documented cases of the emergence of resistance to these drugs by several different sub-strains of avian flu H5N1. Also, the FDA has recently issued a warning label for Tamiflu® after reports of serious psychiatric side-effects in patients receiving the drug, especially children. These factors suggest that there is a significant clinical need for new influenza drugs, with improved properties (including efficacy, selectivity and reduced sensitivity to resistance) relative to the currently marketed drugs.

SUMMARY OF THE INVENTION

In one aspect, the present invention provides a compound of formula (I)

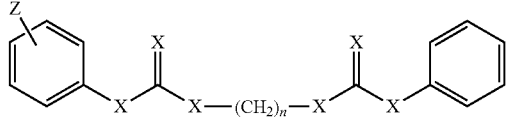

(I)

wherein
n is 1-6:
each X is independently X, NR, or O:
Z may be 1-3 substituents, each of which is independently selected from the group consisting of —C(O)NR$_2$, —C(O)NR$_2$, —C(O)OR, —C$_{1-4}$-alkyl-C(O)OR, —NR$_2$, —C$_{1-4}$-allyl-NR$_2$, —NRC(O)R, —C$_{1-4}$-alkyl-NRC(O)R, —C(O)C$_{1-4}$-alkyl, —C$_{1-4}$-alkyl-C(O)C$_{1-4}$-allyl, —OR, —C$_{1-4}$-alkyl-OR, O—C$_{1-4}$-alkyl-OR, —S(O)$_2$—C$_{1-4}$-alkyl, —S(O)$_2$—NR$_2$, —CF$_3$, C$_{1-4}$-alkyl-CF$_3$, C(O)CF$_3$, C(O)C$_{1-4}$-allyl-CF$_3$, and R; and
each R is independently H or C$_{1-4}$-alkyl:
and pharmaceutically acceptable salts thereof.

In one aspect, the invention also encompasses uses of said compounds for the inhibition of influenza. In one embodiment, compounds of the invention may be used for the treatment or prophylaxis of influenza A, in particular H1N1 or H5N1 influenza.

In one aspect, the invention provides for use of 2-nitro-N-[4-(pyridin-4-ylamino)phenyl]-4-(quinolin-4-ylamino)benzamide for the inhibition of influenza. In one embodiment, said compound may be used for the treatment or prophylaxis of influenza A, in particular H1N1 or H5N1 influenza.

DETAILED DESCRIPTION OF THE INVENTION

Figure 1C:
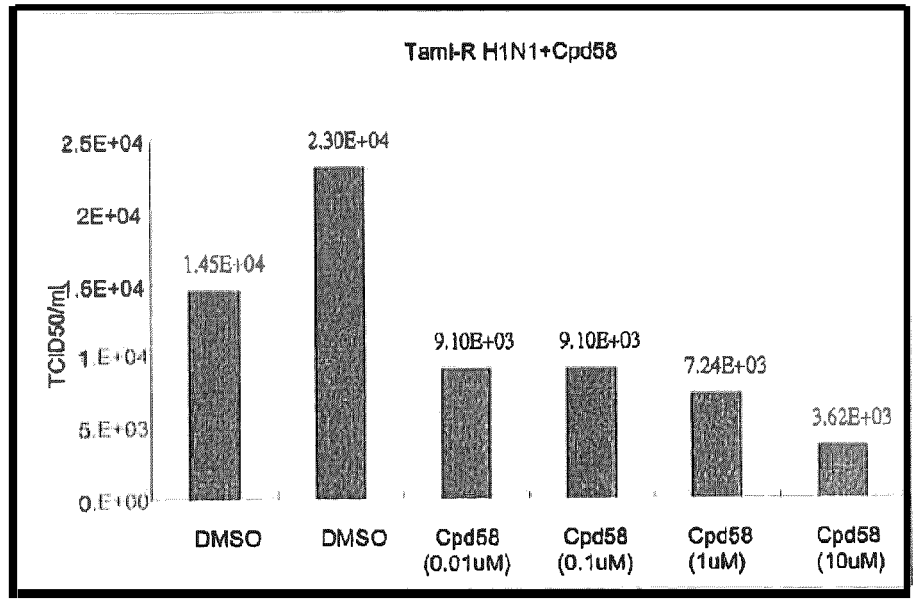
FIG. 1: The effects of Compound 58 versus Tamiflu on Tamiflu-sensitive and Tamiflu-resistant H1N1 influenza viruses is shown. MDCK cells were infected with Tamiflu-sensitive H1N1 (FIGS. 1A, 1B) or Tamiflu-resistant viruses (FIGS. 1C, 1D) at a multiplicity of infection of 0.2.

Compounds:
In one aspect, the present invention provides a compound of formula (I)

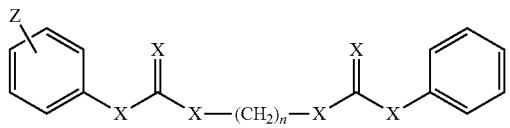

(I)

wherein
n is 1-6:
each X is independently X, NR, or O:
Z may be 1-3 substituents, each of which is independently selected from the group consisting of —C(O)NR$_2$, —C$_{1-4}$-alkyl-C(O)NR$_2$, —C(O)OR, —C$_{1-4}$-alkyl-C(O)

OR, —NR₂, —C₁₋₄-alkyl-NR₂, —NRC(O)R, —C₁₋₄-alkyl-NRC(O)R, —C(O)C₁₋₄-alkyl, —C₁₋₄-alkyl-C(O)C₁₋₄-allyl, —OR, —C₁₋₄-alkyl-OR, O—C₁₋₄-alkyl-OR, —S(O)₂—C₁₋₄-allyl, —S(O)₂—NR₂, —CF₃, C₁₋₄-allyl-CF₃, C(O)CF₃, C(O)C₁₋₄-allyl-CF₃, and R; and
each R is independently H or C₁₋₄-allyl;
and pharmaceutically acceptable salts, solvent, and hydrates thereof.

In one aspect, the present invention provides compounds of formula (Ia)

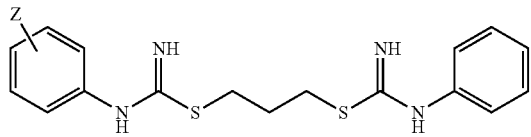

(Ia)

wherein
Z is a substituent selected from the group consisting of —C(O)NR₂, —C₁₋₄-alkyl-C(O)NR₂, —C(O)OR, —C₁₋₄-alkyl-C(O)OR, —NR₂, —NRC(O)R, —C₁₋₄-allyl-NRC(O)R, —C(O)C₁₋₄-alkyl, —C₁₋₄-alkyl-C(O)C₁₋₄-alkyl, —OR, —C₁₋₄-alkyl-OR, O—C₁₋₄-alkyl-OR, —S(O)₂—C₁₋₄-allyl, —S(O)₂—NR₂, —CF₃, C₁₋₄-allyl-CF₃, C(O)CF₃, C(O)C₁₋₄-allyl-CF₃, and R;
and pharmaceutically acceptable salts, solvents, and hydrates thereof.
Z may be —C(O)NH-Me, —S(O)₂-Me₂, —S(O)₂—NH₂, —C(O)OMe, —OCH₂CH₂OMe, —CH₂OMe, NMe₂, C(O)NH₂, C(O)Me, CH₂C(O)OH, CH₂, C(O)NH₂, and C(O)NMe₂.
Examples of Such Compounds are Shown in Table 2.

The compound carbamimidothioic acid, phenyl-, 1,3-propanediyl ester, dihydrobromide is previously known and has CAS Number 852-55-1 (see National Cancer Institute). However, its use for treating influenza is novel.

The compound 2-nitro-N-[4-(pyridin-4-ylamino)phenyl]-4-(quinolin-4-ylamino)benzamide whose structural formula is shown below as Formula II:

Formula II

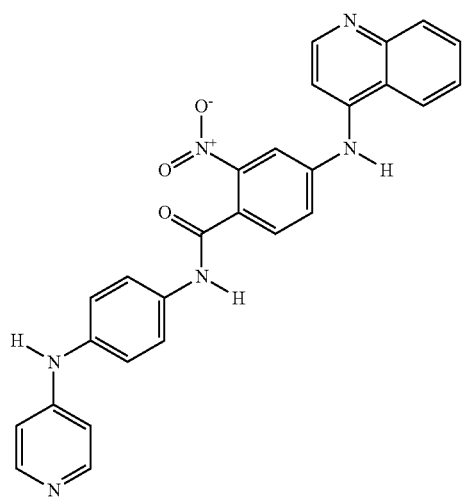

is previously known and has CAS Number 53221-73-1. However, its use for treating influenza is novel.

Salts, Solvates, and Hydrates:

The compounds of this invention optionally comprise salts of the compounds herein. Particular mention may be made of the pharmacologically acceptable salts of inorganic and organic acids customarily used in pharmacy. Those suitable are water-soluble and water-insoluble acid addition salts with acids such as, for example, hydrochloric acid, hydrobromic acid, phosphoric acid, nitric acid, sulfuric acid, acetic acid, citric acid, D-gluconic acid, benzoic acid, 2-(4-hydroxybenzoyl)benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid. Salts with bases are also suitable, including salts with alkali metal (lithium, sodium, potassium) or calcium, aluminum, magnesium, titanium, ammonium, meglumine or guanidinium salts.

It is known to the person skilled in the art that the compounds according to the invention, and also their salts, may contain varying amounts of solvents, for example when they are isolated in crystalline form. The invention therefore also embraces all solvates and in particular all hydrates of the compounds of the formulas I and II and also all solvates and in particular all hydrates of the salts of the compounds of the formulas I and II.

Stereoisomers:

Certain compounds of the invention contain chiral centres. Both racemic and diasteromeric mixtures, as well as the individual optical isomers isolated or synthesized, substantially free of their enantiomeric or diastereomeric partners, are all within the scope of the invention. The racemic mixtures may be separated into their individual, substantially optically pure isomers through well-known techniques, such as the separation of diastereomeric salts formed with optically active adjuncts, e.g., acids or bases followed by conversion back to the optically active substances. The desired optical isomer may be synthesized by means of stereospecific reactions, beginning with the appropriate stereoisomer of the desired starting material.

Prodrugs:

Prodrugs of the compounds of the invention are also contemplated. The terms "pro-drug" and "prodrug" are used interchangeably herein and refer to any compound which releases an active parent drug according to Formula I or Ia or II in vivo when such prodrug is administered to a mammalian subject. Prodrugs of a compound of Formula I or Ia or II are prepared by modifying one or more functional group(s) present in the compound of Formula I or Ia or II in such a way that the modification(s) may be cleaved in vivo to release the parent compound. Prodrugs include compounds of Formula I or Ia or II wherein a hydroxy, amino, carboxy or carbonyl group in a compound of Formula I or Ia or II is bonded to any group that may be cleaved in vivo to regenerate the free hydroxyl, or amino group, respectively. Examples of prodrugs include, but are not limited to, esters (e.g., acetate, dialkylaminoacetates, formates, phosphates, sulfates, and benzoate derivatives) and carbamates (e.g., N,N-dimethylamino carbonyl) of hydroxy functional groups, esters groups (e.g. ethyl esters, morpholinoethanol esters) of carboxyl functional groups, N-acyl derivatives (e.g. N-acetyl) N-Mannich bases, Schiff bases and enaminones of amino functional groups, oximes, acetals, ketals and enol esters of ketone and aldehyde functional groups in compounds of Formula I or Ia or II, and the like, See Bundegaard, H. "Design of Prodrugs" p. 1-92, Elsevier, New York-Oxford (1985).

Pharmaceutical Formulations and Routes of Administration:

The compositions of the present invention may be formulated in a conventional manner using one or more pharmaceutically acceptable carriers. Thus, the active compounds of the invention may be formulated for oral, buccal, intranasal, parenteral (e.g., intravenous, intramuscular or subcutaneous), topical or rectal administration or in a form suitable for administration by inhalation.

For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, methyl cellulose or hydrogenated edible fats); emulsifying agents (e.g., lecithin or acacia); non-aqueous vehicles (e.g., almond oil, oily esters or ethyl alcohol); and preservatives (e.g., methyl or propyl p-hydroxybenzoates or sorbic acid).

For buccal administration, the composition may take the form of tablets or lozenges formulated in a conventional manner.

The compounds of the invention can also be formulated for sustained delivery according to methods well known to those of ordinary skill in the art. Examples of such formulations can be found in U.S. Pat. Nos. 3,538,214; 4,060,598; 4,173,626; 3,119,742; and 3,492,397, which are incorporated herein by reference in their entirety.

The compounds of the invention may be formulated for parenteral administration by injection, including using conventional catheterization techniques or infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulating agents such as suspending, stabilizing and/or dispersing agents. Alternatively, the active ingredient may be in a powder form for reconstitution with a suitable vehicle, e.g., sterile pyrogen-free water, before use.

The compounds of the invention may also be formulated in rectal compositions such as suppositories or retention enemas, e.g., containing conventional suppository bases such as cocoa butter or other glycerides.

For intranasal administration or administration by inhalation, the active compounds of the invention are conveniently delivered in the form of a solution, dry powder formulation or suspension from a pump spray container that is squeezed or pumped by the patient or as an aerosol spray presentation from a pressurized container or a nebulizer, with the use of a suitable propellant, e.g., dichlorodifluoromethane, trichlorofluoromethane, dichlorotetrafluoroethane, heptafluoroalkanes, carbon dioxide or other suitable gas. In the case of a pressurized aerosol, the dosage unit may be determined by providing a valve to deliver a metered amount. The pressurized container or nebulizer may contain a solution or suspension of the active compound. Capsules and cartridges (made, for example, from gelatin) for use in an inhaler or insufflator may be formulated containing a powder mix of a compound of the invention and a suitable powder base such as lactose or starch.

The compound of the invention including pharmaceutically acceptable salts and solvates thereof may be used on their own but will generally be administered in the form of a pharmaceutical composition in which the compound (active ingredient) is in association with a pharmaceutically acceptable adjuvant, diluent or carrier. Depending on the mode of administration, the pharmaceutical composition will preferably comprise from 0.05 to 99% w (percent by weight), more preferably from 0.10 to 70% w, of active ingredient, and, from 1 to 99.95% w, more preferably from 30 to 99.90% w, of a pharmaceutically acceptable adjuvant, diluent or carrier, all percentages by weight being based on total composition.

"Pharmaceutically acceptable excipient" means an excipient that is useful in preparing a pharmaceutical composition that is generally safe, non-toxic and neither biologically nor otherwise undesirable, and includes excipient that is acceptable for veterinary use as well as human pharmaceutical use. A "pharmaceutically acceptable excipient" as used in the specification and claims includes both one and more than one such excipient.

Uses of the Compounds:

The compounds of this invention, including the compounds of Formula I, Ia, and IL are useful in the prophylaxis of influenza infections or treatment of existing influenza infections in animals such as duck, rodents, or swine, or in man. This includes influenza A (such as the group-1 type neuraminidases including H1N1 and H5N1, and the group-2 neuraminidases including H1N2, H3N2, H2N3, H7N7, and H9N2), influenza B, and influenza C. The compounds may be especially useful in instances of drug-resistance to other influenza medications, such as adamantanes (e.g. amantadine and rimantadine) and neuraminidase inhibitors (e.g. oseltamivir and zanamivir).

The compounds disclosed herein, including the compounds of Formula I, Ia, and II, may be used to inhibit viral RNA-dependent RNA polymerase.

EXPERIMENTAL

Carbamimidothioic acid, phenyl-, 1,3-propanediyl ester, dihydrobromide, referred to herein as Compound 58:

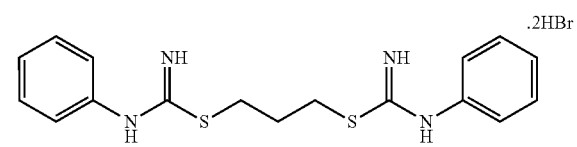 [SMILES: N=C(Nc1ccccc1)SCCCSC(=N)Nc1ccccc1]

This compound was obtained from the National Cancer Institute, USA.

2-nitro-N-[4-(pyridin-4-ylamino)phenyl]-4-(quinolin-4-ylamino)benzamide (also known as 2-(hyroxy(oxido)amino-N-(4-(4-pyridinylamino)phenyl)-4-(4-quinolinylamino)benzaminde), referred to herein as Compound 73.

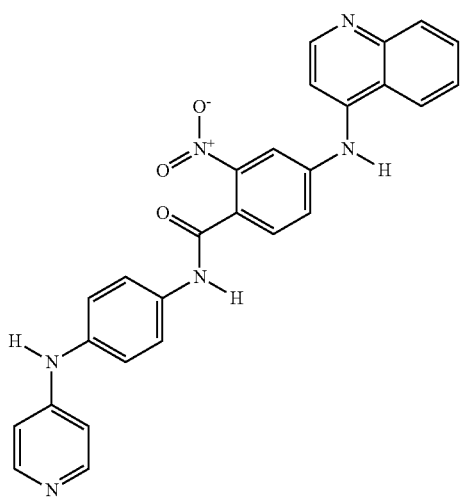 [SMILES: O=C(Nc1ccc(Nc2ccncc2)cc1)c1ccc(Nc2ccnc3ccccc23)cc1[N+](=O)[O-]]

This compound was obtained from the National Cancer Institute, USA.

Cell Viability Test:

MDCK cells were seeded at $2\times10^6$/ml in a 96-well plate for 16-24 hours. Compound 58 (50 uM) was added to the cells. DMSO was added to the cells as a control. Cells were incubated at 37° C. and 5% $CO_2$ for 72 hours, and then Thiazolyl Blue Tetrazolium Bromide (MTT) was added to a final concentration of 0.1 mg/ml. After two hours, the culture supernatant was removed and each well was replenished with isopropanol. The MTT metabolic product, formazan, was dissolved in isopropanol for five minutes with shaking. The optical densities of formazan and background were measured at 560 nm and 670 nm, respectively. The cytotoxicity index was calculated as follows:

$$(\lambda 560_{sample1} - \lambda 670_{sample1})/(\lambda 560_{DMSO} - \lambda 670_{DMSO})$$

Compound 58 at 50 uM does not display cytotoxicity in MDCK cells compared with those treated with DMSO.

|  | Cytotoxicity index |
|---|---|
| Cpd 58 (50 uM) | 0.916 |
| DMSO | 1.0 |

Viral Infection:

Human influenza H1N1 virus (A/HK/54/98 (Tamiflu-sensitive strain) and A/Vicotria/07159200/07 (Tamiflu-resistant strain)), H9N2 (A/Quail/HK/G1/97), and H3N2 (A/H3N2/1174/99) were prepared as described in previous reports (Lee D C, Cheung C Y, Law A H, Mok C K, Peiris M, Lau A S., J Virol. 2005 August; 79(16):10147-54; and Mok C K, Lee D C, Cheung C Y, Peiris M, Lau A S., J Gen Virol. 2007 April; 88(Pt 4):1275-80). Madin-Darby canine kidney (MDCK) cells were infected with viruses at a multiplicity of infection (m.o.i.) of 2 for 30 min and the virus containing supernatants were removed and washed once with PBS. Serum Free Medium supplemented with N-tosyl-L-phenylalanyl chloromethyl ketone (TPCK)-trypsin and compounds were used to replenish the cell culture. The supernatants and virus-infected cells were harvested for $TCID_{50}$ assays.

Tissue Culture Infective Dose ($TCID_{50}$) Determination:

Prior to TCID assays, MDCK cells were seeded at $2\times10^4$ cells per well on the 96-well plates. Culture supernatants were harvested from virus-infected cells at 48-hour post-infection. Serial two-fold dilutions of the supernatant samples were prepared and the diluted samples were incubated with the MDCK cells for one hour (37° C., 5% $CO_2$) for virus adsorption. The virus inoculum was then removed. Cells were washed once and replenished with minimum essential medium (MEM), supplemented with 1 ug/ml N-tosyl-L-phenylalanyl chloromethyl ketone (TPCK)-treated trypsin. After four days of incubation (37° C., 5% $CO_2$), cells were fixed with 10% formaldehyde for 30 minutes and stained with 0.5% crystal violet to determine the virus-induced cytopathic effects. $TCID_{50}$ titers were calculated using the Reed-Muench formula (Methods and Techniques in Virology (1993), edited by Payment P and Trudel M, Marcel Dekker Inc. pp. 32-33).

Figure 1D:
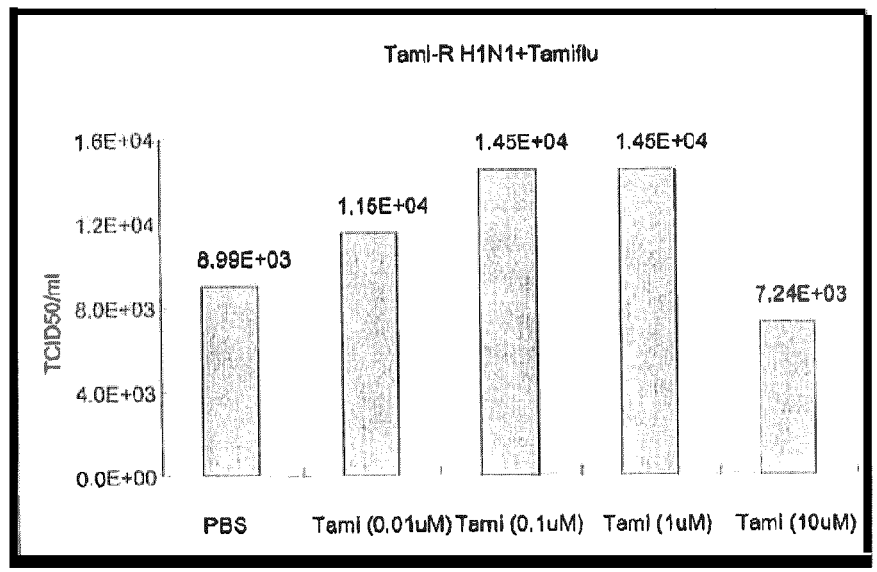

The dosage effects of Compound 58 on H1N1 (A/HK/54/98), H9N2, and H3N2 influenza viral titers is shown in Table 1A. The dosage effects of Compound 73 on H1N1 (A/HK/54/98) influenza viral titers is shown in Table 1B. The dosage effect of Compound 58 on H1N1 (A/HK/54/98) vs. H1N1 (A/Vicotria/07159200/07) is shown in FIG. 1.

TABLE 1A

Dosage effects of Compound 58 on influenza viral titers.

| Concentration | $TCID_{50}$/ml | | |
|---|---|---|---|
| (μM) | H1N1 virus[A] | H9N2 virus[B] | H3N2 virus[C] |
| 0 (DMSO) | $1.38 \times 10^5$ | $3.04 \times 10^3$ | $3.44 \times 10^4$ |
| 0 (DMSO) | $1.84 \times 10^5$ | $2.15 \times 10^3$ | $5.79 \times 10^4$ |
| 10 | $2.90 \times 10^4$ | $1.14 \times 10^3$ | $4.61 \times 10^4$ |
| 20 | $1.82 \times 10^4$ | $4.16 \times 10^2$ | $1.72 \times 10^4$ |
| 50 | $4.53 \times 10^2$ | $1.90 \times 10^2$ | $7.24 \times 10^3$ |
| 50 (Tamiflu) | $1.45 \times 10^4$ | $9.00 \times 10^1$ | $7.24 \times 10^3$ |

[A] MDCK cells were infected with H1N1 virus at an m.o.i of 2. Cells were then incubated with Compound 58 at various concentrations as indicated, or with Tamiflu (control drug) at 50 uM as the standard antiviral agent. Two controls with no Compound 58 were also run. Culture supernatants were collected at 48-hour post-infection. Viral titers ($TCID_{50}$) were measured by titration in MDCK cells. (Representative results from three experiments).
[B] Results on H9N2 virus. MDCK cells were infected with H9N2 virus at an m.o.i of 2. Cells were then incubated with Compound 58 at various concentrations as indicated, or with Tamiflu (control drug) at 50 uM as the standard antiviral agent. Two controls with no Compound 58 were also run. Culture supernatants were collected at 48-hour post-infection. Viral titers ($TCID_{50}$) were measured by titration in MDCK cells. (Representative results from three experiments).
[C] Results on H3N2 virus. MDCK cells were infected with H3N2 virus at an m.o.i of 2. Cells were then incubated with Compound 58 at various concentrations as indicated, or with Tamiflu (control drug) at 50 uM as the standard antiviral agent. Two controls with no Compound 58 were also run. Culture supernatants were collected at 48-hour post-infection. Viral titers ($TCID_{50}$) were measured by titration in MDCK cells. (Representative results from three experiments).

The $TCID_{50}$ results demonstrate that Compound 58 inhibits the replication of the H1N1, the H9N2, and the H3N2 viruses in a significant manner, and at a level comparable to that of Tamiflu. Compound 58 appears to be particularly effective against H1N1 as compared with Tamiflu.

TABLE 1B

Dosage effects of Compound 73 on influenza viral titers.

| Concentration (μM) | $TCID_{50}$/ml H1N1 virus[A] |
|---|---|
| 0 (DMSO) | $2.44 \times 10^4$ |
| 0 (DMSO) | $3.64 \times 10^4$ |
| 100 | $2.28 \times 10^3$ |
| 100 (Tamiflu) | $1.52 \times 10^3$ |

[A] MDCK cells were infected with H1N1 virus at an m.o.i of 2. Cells were then incubated with Compound 73 at various concentrations as indicated, or with Tamiflu (control drug) at 100 uM as the standard antiviral agent. Two controls with no Compound 73 were also run. Culture supernatants were collected at 48-hour post-infection. Viral titers ($TCID_{50}$) were measured by titration in MDCK cells. (Representative results from three experiments).

H1N1 virus (tamiflu-sensitive) was inhibited by Compound 73. The virus level was suppressed by around 10 fold.

With regard to FIG. 1, the effects of Compound 58 on Tamiflu-sensitive and Tamiflu-resistant H1N1 influenza viruses is shown. MDCK cells were infected with Tamiflu-sensitive H1N1 (A, B) or Tamiflu-resistant viruses (C, D) at a multiplicity of infection of 0.2. Cells were then incubated with compound 58 (A, C) or Tamiflu (B, D) at various concentrations as indicated. Culture supernatants were collected at 48-hour post-infection. Viral titers (TCID50) were measured by titration in MDCK cells as described above. Tami-R=Tamiflu resistant.

The viral titers of Tamiflu-sensitive (Tami-S) H1N1 virus decreased by 5-fold and 8-fold with compound 58 and Tamiflu treatment, respectively. Of note, for cells infected with Tamiflu-resistant (Tami-R) H1N1 virus, Tamiflu treatment had minimal effects on the viral titers. For example, even at 10 uM of Tamiflu, the Tami-R H1N1 viral titers only decreased by 20%. In contrast, the viral titer of Tami-R H1N1-infected cells decreased by 4-fold with compound 58 treatment. Hence, compound 58 showed potent inhibitory effects against both Tami-S and Tami-R H1N1 viruses.

TABLE 2

Examples of compounds of the invention

TABLE 2-continued

Examples of compounds of the invention

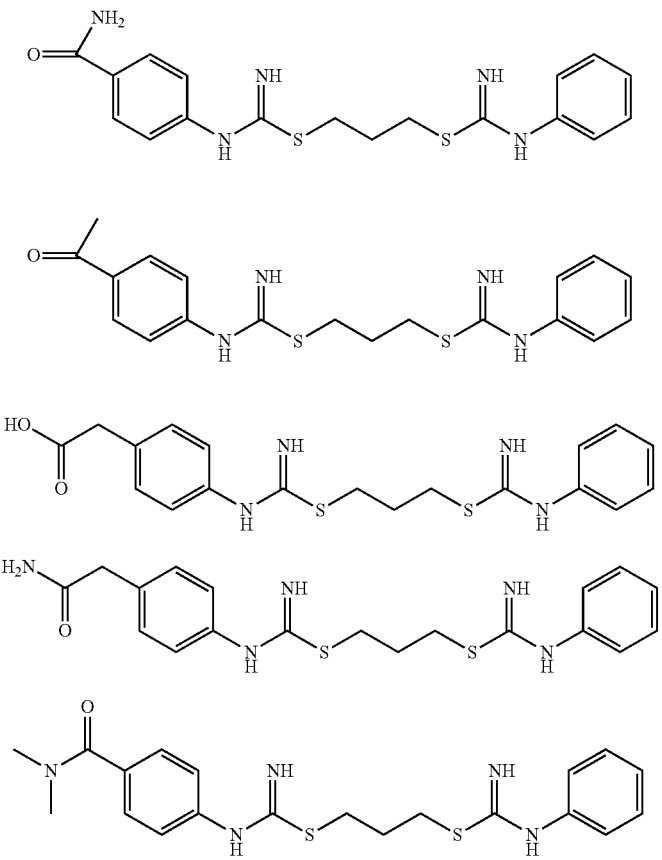

The invention claimed is:

1. A method for the treatment of influenza, comprising administering to a patient a compound of formula (I):

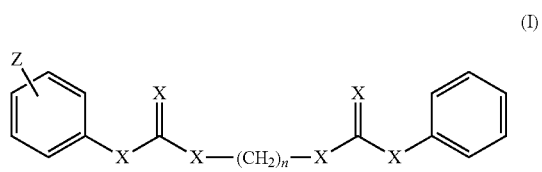

wherein
n is 1-6;
each X is independently S, NR, or O;
Z may be 1-3 substituents, each of which is independently selected from the group consisting of —C(O)NR$_2$, —C$_{1-4}$-alkyl-C(O)NR$_2$, —C(O)OR, —C$_{1-4}$-alkyl-C(O)OR, —NR$_2$, —C$_{1-4}$-alkyl-NR$_2$, —NRC(O)R, —C$_{1-4}$-alkyl-NRC(O)R, —C(O)C$_{1-4}$-alkyl, —C$_{1-4}$-alkyl-C(O)C$_{1-4}$-alkyl, —OR, —C$_{1-4}$-alkyl-OR, O—C$_{1-4}$-alkyl-OR, —S(O)$_2$—C$_{1-4}$-alkyl, —S(O)$_2$—NR$_2$, —CF$_3$, C$_{1-4}$-alkyl-CF$_3$, C(O)CF$_3$, C(O)C$_{1-4}$-alkyl-CF$_3$, and R; and
each R is independently H or C$_{1-4}$-alkyl;
or a pharmaceutically acceptable salt, solvent, or hydrate thereof.

2. The method of claim 1, comprising administering carbamimidothioic acid, phenyl-, 1,3-propanediyl ester or a pharmaceutically acceptable salt, solvent, or hydrate thereof to a patient.

3. A method for the treatment of influenza, comprising administering carbamimidothioic acid, phenyl-, 1,3-propanediyl ester, dihydrobromide or 2-nitro-N-[4-(pyridin-4-ylamino)phenyl]-4-(quinolin-4-ylamino)benzamide to a patient.

4. The method according to claim 2, wherein the influenza is influenza A.

5. The method according to claim 2, wherein the influenza is influenza type B or C.

6. The method according to claim 4, wherein the influenza is type A group-1.

7. The method according to claim 4, wherein the influenza is type A group-2.

8. The-method according to claim 4, wherein the influenza is H1N1, H1N2, H3N2, H5N1, H9N2, H7N3, or H7N7.

9. The-method according to claim 2, for treatment of Type A H5N1 influenza.

10. The method according to claim 2, for treatment of Type A H1N1 influenza.

11. The method for the inhibition of a viral RNA-dependent RNA polymerase, comprising administering a compound of formula (I)

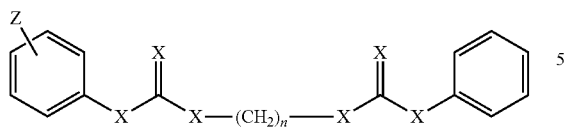

(I)

wherein
n is 1-6;
each X is independently S, NR, or O;
Z may be 1-3 substituents, each of which is independently selected from the group consisting of —C(O)NR$_2$, —C$_{1-4}$-alkyl-C(O)NR$_2$, —C(O)OR, —C$_{1-4}$-alkyl-C(O)OR, —NR$_2$, —C$_{1-4}$-alkyl-NR$_2$, —NRC(O)R, —C$_{1-4}$-alkyl-NRC(O)R, —C(O)C$_{1-4}$-alkyl, —C$_{1-4}$-alkyl-C(O)C$_{1-4}$-alkyl, —OR, —C$_{1-4}$-alkyl-OR, O—C$_{1-4}$-alkyl-OR, —S(O)$_2$—C$_{1-4}$-alkyl, S(O)$_2$—NR$_2$, —CF$_3$, C$_{1-4}$-alkyl-CF$_3$, C(O)CF$_3$, C(O)C$_{1-4}$-alkyl-CF$_3$, and R; and
each R is independently H or C$_{1-4}$-alkyl;
and pharmaceutically acceptable salts, solvents, and hydrates thereof.

12. A method for the inhibition of a viral RNA-dependent RNA polymerase, comprising administering carbamimidothioic acid, phenyl-, 1,3-propanediyl ester, dihydrobromide or 2-nitro-N-[4-(pyridin-4-ylamino)phenyl]-4-(quinolin-4-ylamino)benzamide.

13. The method according to claim 1, for the treatment of a drug-resistant strain of influenza.

14. The method according to claim 13, wherein the drug-resistant strain is resistant to oseltamivir or zanamivir.

* * * * *